United States Patent
Min

(10) Patent No.: US 8,396,567 B2
(45) Date of Patent: Mar. 12, 2013

(54) IMPLANTABLE MEDICAL DEVICE LEAD WITH INDUCTIVE-CAPACITIVE FILTERS HAVING INDUCTORS WITH PARALLEL CAPACITORS TO REDUCE LEAD HEATING DURING MRI

(75) Inventor: Xiaoyi Min, Thousand Oaks, CA (US)

(73) Assignee: Pacsetter, Inc., Sylmar, CA (US)

( * ) Notice: Subject to any disclaimer, the term of this patent is extended or adjusted under 35 U.S.C. 154(b) by 297 days.

(21) Appl. No.: 12/955,692

(22) Filed: Nov. 29, 2010

(65) Prior Publication Data

US 2012/0136421 A1     May 31, 2012

(51) Int. Cl.
 *A61N 1/16* (2006.01)
(52) U.S. Cl. ......... 607/119; 607/115; 607/116; 333/182
(58) Field of Classification Search .................. 607/119, 607/115, 116
See application file for complete search history.

(56) References Cited

U.S. PATENT DOCUMENTS

| | | | |
|---|---|---|---|
| 4,746,864 A | 5/1988 | Satoh | |
| 5,063,348 A | 11/1991 | Kuhara et al. | |
| 6,871,091 B2 | 3/2005 | Wilkinson et al. | |
| 6,944,489 B2 | 9/2005 | Zeijlemaker et al. | |
| 2005/0222659 A1 | 10/2005 | Olsen et al. | |
| 2006/0229693 A1 | 10/2006 | Bauer et al. | |
| 2007/0112398 A1 | 5/2007 | Stevenson et al. | |
| 2008/0033497 A1 | 2/2008 | Bulkes et al. | |
| 2008/0116997 A1* | 5/2008 | Dabney et al. | 333/182 |
| 2008/0132986 A1 | 6/2008 | Gray et al. | |
| 2008/0269591 A1 | 10/2008 | Halperin et al. | |
| 2009/0281592 A1* | 11/2009 | Vase | 607/37 |
| 2010/0106214 A1 | 4/2010 | Min | |
| 2010/0106227 A1 | 4/2010 | Min et al. | |
| 2010/0121179 A1 | 5/2010 | Min | |
| 2010/0138192 A1 | 6/2010 | Min | |

* cited by examiner

*Primary Examiner* — Christopher D Koharski
*Assistant Examiner* — Michael Carey

(57) ABSTRACT

To provide radio-frequency (RF) bandstop filtering within an implantable lead for use in reducing lead heating during magnetic resonance imaging (MRI) procedures, parallel inductive-capacitive (LC) filters are provided within the lead. In one example, the ring electrode of the lead is configured to function as one of the capacitive elements of the parallel LC filter to help provide LC bandstop filtering along the ring conductor of the lead. In another example, capacitive plates are provided that sandwich an inductor mounted near the tip of the lead to provide parallel LC bandstop filtering along the tip conductor of the lead.

21 Claims, 10 Drawing Sheets

IMPLANTABLE MEDICAL DEVICE LEAD WITH INDUCTIVE-CAPACITIVE FILTERS HAVING INDUCTORS WITH PARALLEL CAPACITORS TO REDUCE LEAD HEATING DURING MRI

FIELD OF THE INVENTION

The invention generally relates to leads for use with implantable medical devices, such as pacemakers or implantable cardioverter-defibrillators (ICDs) and, in particular, to components for use within such leads to reduce heating during magnetic resonance imaging (MRI) procedures.

BACKGROUND OF THE INVENTION

MRI is an effective, non-invasive magnetic imaging technique for generating sharp images of the internal anatomy of the human body, which provides an efficient means for diagnosing disorders such as neurological and cardiac abnormalities and for spotting tumors and the like. Briefly, the patient is placed within the center of a large superconducting magnetic that generates a powerful static magnetic field. The static magnetic field causes protons within tissues of the body to align with an axis of the static field. A pulsed radio-frequency (RF) magnetic field is then applied causing the protons to begin to precess around the axis of the static field. Pulsed gradient magnetic fields are then applied to cause the protons within selected locations of the body to emit RF signals, which are detected by sensors of the MRI system. Based on the RF signals emitted by the protons, the MRI system then generates a precise image of the selected locations of the body, typically image slices of organs of interest.

However, MRI procedures are problematic for patients with implantable medical devices such as pacemakers and ICDs. One of the significant problems or risks is that the strong RF fields of the MRI can induce currents through the lead system of the implantable device into the surrounding tissue, resulting in Joule heating in the cardiac tissue around the electrodes of leads and potentially damaging adjacent tissue. Indeed, the temperature at the tip of an implanted lead has been found to increase as much as 60° Celsius (C.) during an MRI test with the lead immersed in a gel phantom in a non-clinical configuration. Although such a dramatic increase is probably unlikely within a clinical system wherein leads are properly implanted, even a temperature increase of only about 8°-13° C. might cause myocardial tissue damage.

Furthermore, any significant heating of cardiac tissue near lead electrodes can affect the pacing and sensing parameters associated with the tissue near the electrode, thus potentially preventing pacing pulses from being properly captured within the heart of the patient and/or preventing intrinsic electrical events from being properly sensed by the device. The latter might result, depending upon the circumstances, in therapy being improperly delivered or improperly withheld. Another significant concern is that any currents induced in the lead system can potentially generate voltages within cardiac tissue comparable in amplitude and duration to stimulation pulses and hence might trigger unwanted contractions of heart tissue. The rate of such contractions can be extremely high, posing significant clinical risks to patients. Therefore, there is a need to reduce heating in the leads of implantable medical devices, especially pacemakers and ICDs, and to also reduce the risks of improper tissue stimulation during an MRI, which is referred to herein as MRI-induced pacing.

Various techniques have been developed to address these or other related concerns. See, for example, the following patents and patent applications: U.S. patent application Ser. No. 11/943,499, filed Nov. 20, 2007, of Zhao et al., entitled "RF Filter Packaging for Coaxial Implantable Medical Device Lead to Reduce Lead Heating during MRI" (abandoned); U.S. Published Patent Application 2009/0281592, filed May 8, 2008, of Vase, entitled "Shaft-mounted RF Filtering Elements for Implantable Medical Device Lead to Reduce Lead Heating During MRI"; U.S. patent application Ser. No. 11/860,342, filed Sep. 27, 2007, of Min et al., entitled "Systems and Methods for using Capacitive Elements to Reduce Heating within Implantable Medical Device Leads during an MRI"; U.S. patent application Ser. No. 12/042,605, filed Mar. 5, 2009, of Mouchawar et al., entitled "Systems and Methods for using Resistive Elements and Switching Systems to Reduce Heating within Implantable Medical Device Leads during an MRI"; and U.S. patent application Ser. No. 11/963,243, filed Dec. 21, 2007, of Vase et al., entitled "MEMS-based RF Filtering Devices for Implantable Medical Device Leads to Reduce Lead Heating during MRI."

See, also, U.S. patent application Ser. No. 12/257,263, filed Oct. 23, 2008, of Min, entitled "Systems and Methods for Exploiting the Ring Conductor of a Coaxial Implantable Medical Device Lead to provide RF Shielding during an MRI to Reduce Lead Heating"; U.S. Published Patent Application 2010/0106227, filed Oct. 23, 2008, of Min, entitled "Systems and Methods for Disconnecting Electrodes of Leads of Implantable Medical Devices during an MRI to Reduce Lead Heating while also providing RF Shielding"; U.S. Published Patent Application 2010/0121179, of Min et al., filed Nov. 13, 2008, entitled "Systems And Methods For Reducing RF Power or Adjusting Flip Angles During an MRI For Patients with Implantable Medical Devices"; and U.S. Published Patent Application 2010/0106214 of Min et al., filed Oct. 23, 2008, entitled "Systems and Methods for Exploiting the Tip or Ring Conductor of an Implantable Medical Device Lead during an MRI to Reduce Lead Heating and the Risks of MRI-Induced Stimulation".

At least some of these techniques are directed to installing RF filters, such as inductive (L) filters or inductive-capacitive (LC) filters, within the leads for use in filtering signals at frequencies associated with the RF fields of MRIs. It is particularly desirable to select or control the inductance (L), parasitic capacitance (Cs) and parasitic resistance (Rs) of such devices to attain a high target impedance (e.g. at least 1000 ohms) at RF to achieve effective heat reduction. See, for example, U.S. patent application Ser. No. 11/955,268, filed Dec. 12, 2007, of Min, entitled "Systems and Methods for Determining Inductance and Capacitance Values for use with LC Filters within Implantable Medical Device Leads to Reduce Lead Heating during an MRI"; U.S. Published Patent Application 2010/0138192, of Min et al., filed Dec. 1, 2008, entitled "Systems and Methods for Selecting Components for Use in RF Filters within Implantable Medical Device Leads based on Inductance, Parasitic Capacitance and Parasitic Resistance."

Although these techniques are helpful in reducing lead heating due to MRI fields, there is room for further improvement. In particular would be desirable to provide for LC filtering with smaller package size and/or better electrical and mechanical reliability. It is to these ends that aspects of the invention are generally directed.

SUMMARY OF THE INVENTION

In accordance with an exemplary embodiment of the invention, a lead is provided for use with an implantable medical device for implant within a patient. The lead includes an electrode for placement adjacent patient tissues, with at least a portion of the electrode forming a capacitive element; a conductor operative to route signals along the lead between the electrode and the implantable medical device; and an inductive element provided in parallel with the conductor to provide to provide an LC bandstop configured to filter RF signals. By forming a capacitive element using at least a portion of the electrode, LC bandstop filtering can be conveniently provided to reduce lead heating during MRI imaging while maintaining small size package and achieving a relatively high level of electrical and mechanical reliability.

In an illustrative example, wherein the lead is a coaxial bipolar lead for use with a pacemaker or ICD, the electrode that forms at least a portion of the capacitive element is the ring electrode of the lead. More specifically, the coaxial lead has an inner tip conductor leading to a tip electrode at a distal end of the lead and also has an outer ring conductor leading to a ring electrode at the distal end of the lead. The capacitive element of the ring electrode is configured to encircle portions of an inductor to provide LC filtering at the location of a ring electrode. Depending upon the implementation, the inductor can be coiled or spiral and can be formed on printed ceramics or other dielectric substrates (such as with a hollow or donut-shaped core.)

In another embodiment, a capacitive element is instead provided for use with the tip conductor of the lead to provide LC filtering within a tip assembly. For example, the capacitive element may be configured with first and second circular plates mounted parallel to one another (and perpendicular to the axis of the lead) near the distal end of a coaxial lead. The first of the plates is electrical coupled to the distal end of the tip conductor of the lead. The second of the plates is electrically coupled to a helical tip electrode. An inductive coil is mounted between the first and second plates. With this configuration, the first and second plates sandwich the inductive coil, again providing for parallel LC bandpass filtering. In one particular example, electrical connection between the inductive coil and the plates of the capacitive element is provided via a set of mounting shafts or cores, on which the ends of the wires of the inductive element are wrapped.

With appropriate selection of the size, shape and configuration of the various components (such as the number of turns of the inductive coils and the relative size and spacing of the capacitive and inductive components), a desired amount of LC bandstop filtering can typically be achieved at 64 MHz or at 128 MHz to provide heat reduction during MRIs. (It should be understood that 64 MHz and 128 MHz are merely approximate values for the MRI RF frequencies. More precisely, MRIs typically operate at 63.7±0.345 MHz with 1.5 T and at 125.6±3.6 MHz with 3.0 T.) LC filters might be provided along the lead both at the ring and near the tip with different configurations to achieve filtering at both 64 MHz and at 128 MHz. For example, ring electrode LC filter (having coaxially mounted capacitive elements) and a tip assembly LC filter (having capacitive "sandwich" plates mounted perpendicular the axis of the lead) can both be provided. These may be configured to provide LC bandstop filtering at different frequencies, such as one at about 64 MHz and the other at about 128 MHz.

The use of these parallel LC filter designs is particularly well-suited for use with bipolar coaxial cardiac pacing/sensing leads for use with pacemakers and ICDs but may also be employed in connection with other cardiac pacing/sensing leads, such as co-radial leads, or with leads for use with other implantable medical devices.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of MRI System

Figure 1:
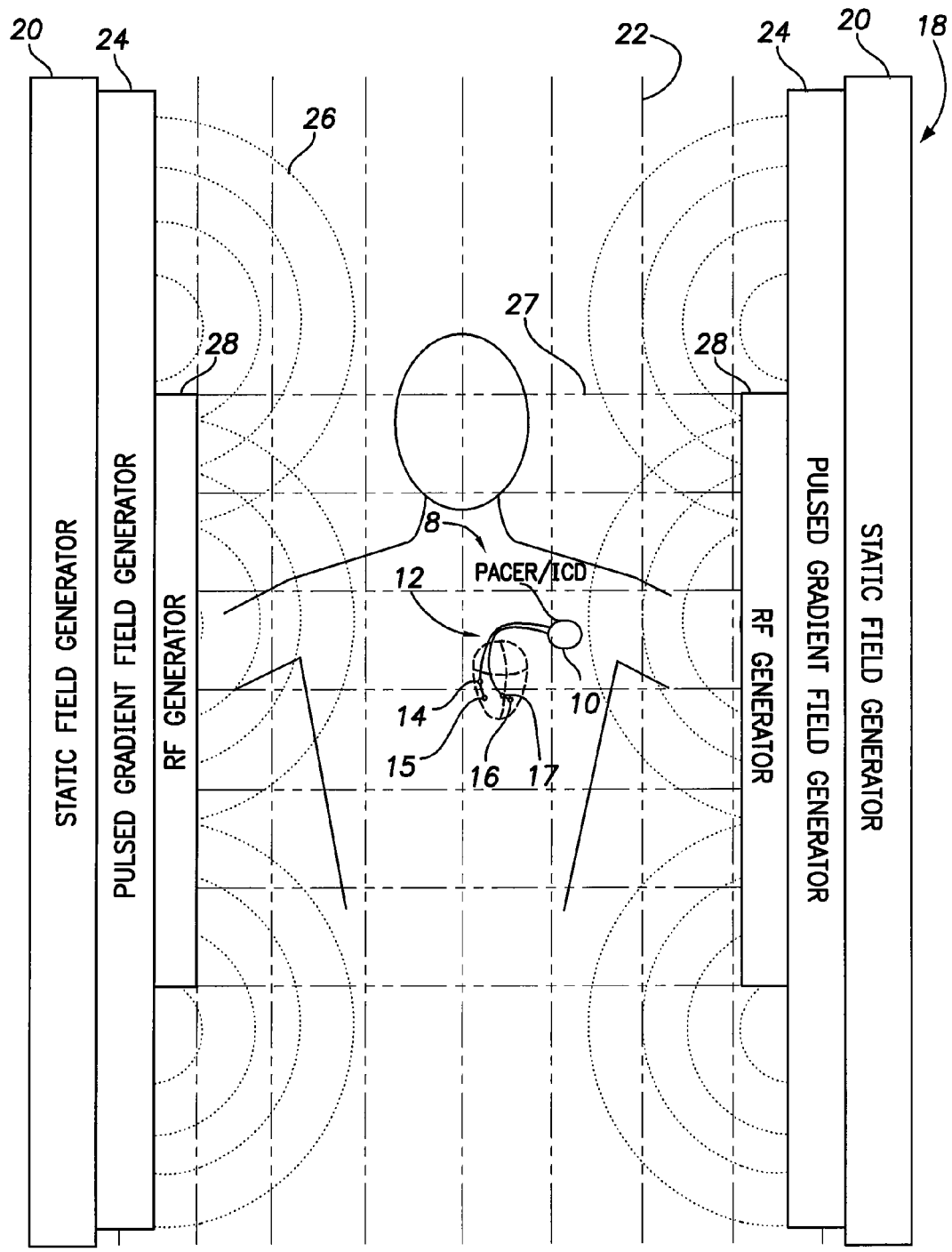
FIG. 1 is a stylized representation of an MRI system along with a patient with a pacer/ICD implanted therein with bipolar RV and LV leads employing parallel LC filters (not specifically shown in FIG. 1) near their distal ends.
Figure 9:
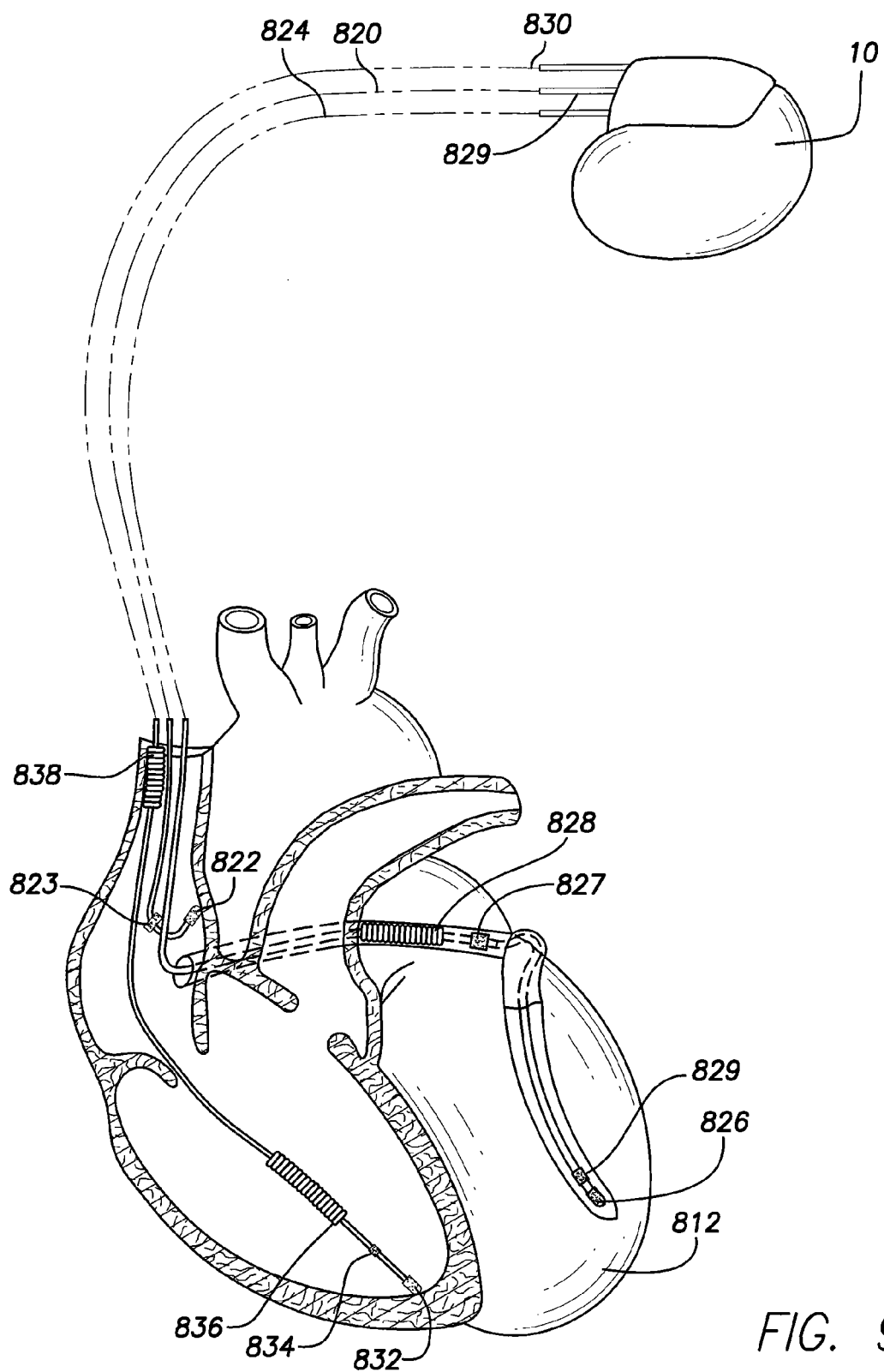
FIG. 9 is a simplified, partly cutaway view, illustrating the pacer/ICD of FIG. 1 (without any coiling of the leads around the device), along with a more complete set of leads implanted in the heart of the patient, wherein the RV and LV leads include parallel LC bandstop filtering devices near distal ends of the leads.

FIG. 1 illustrates an implantable medical system 8 having a pacer/ICD 10 for use with a set of bipolar pacing/sensing leads 12, which include tip and ring electrodes 14, 15, 16 and 17, as shown, wherein parallel LC RF filtering elements are coupled to (and formed with) the ring electrodes, 14 and 16, or mounted near the tip electrodes, 15, 17. That is, in one example, coaxial parallel LC filtering elements are integrated with the ring electrodes of the respective leads. In another example, the parallel LC filtering elements are configured using a sandwich design for mounting near the tip of the lead. In either case, the parallel LC filtering elements help reduce lead heating during an MRI scan generated by MRI system 18. (In FIG. 1, only two leads are shown, a right ventricular (RV) lead and a left ventricular (LV) lead. A more complete lead system is illustrated in FIG. 9, described below.) In some implementations, one or more additional leads may be provided (such as a right atrial (RA) lead). Parallel LC filters may be provided within the additional leads as well. Alternatively, in some implementations, no LV lead is provided.

As to the MRI system 18, the system includes a static field generator 20 for generating a static magnetic field 22 and a pulsed gradient field generator 24 for selectively generating pulsed gradient magnetic fields 26. The MRI system also includes an RF generator 28 for generating RF fields 27. Other components of the MRI, such as its sensing and imaging components are not shown. MRI systems and imaging techniques are well known and will not be described in detail herein. For exemplary MRI systems see, for example, U.S. Pat. No. 5,063,348 to Kuhara, et al., entitled "Magnetic Resonance Imaging System" and U.S. Pat. No. 4,746,864 to Satoh, entitled "Magnetic Resonance Imaging System." Note that the fields shown in FIG. 1 are stylized representations of the MRI fields intended merely to illustrate the presence of the fields. Actual MRI fields generally have far more complex patterns.

Thus, the leads of pacer/ICD 10 include parallel LC RF filtering elements. The parallel LC filtering configurations described herein address the packaging issues discussed above, such as by providing for a generally small packaging size and/or improving electrical and mechanical reliability.

With reference to the remaining figures, various examples of parallel LC filtering configurations will be described in greater detail.

Lead Overview

Figure 2:
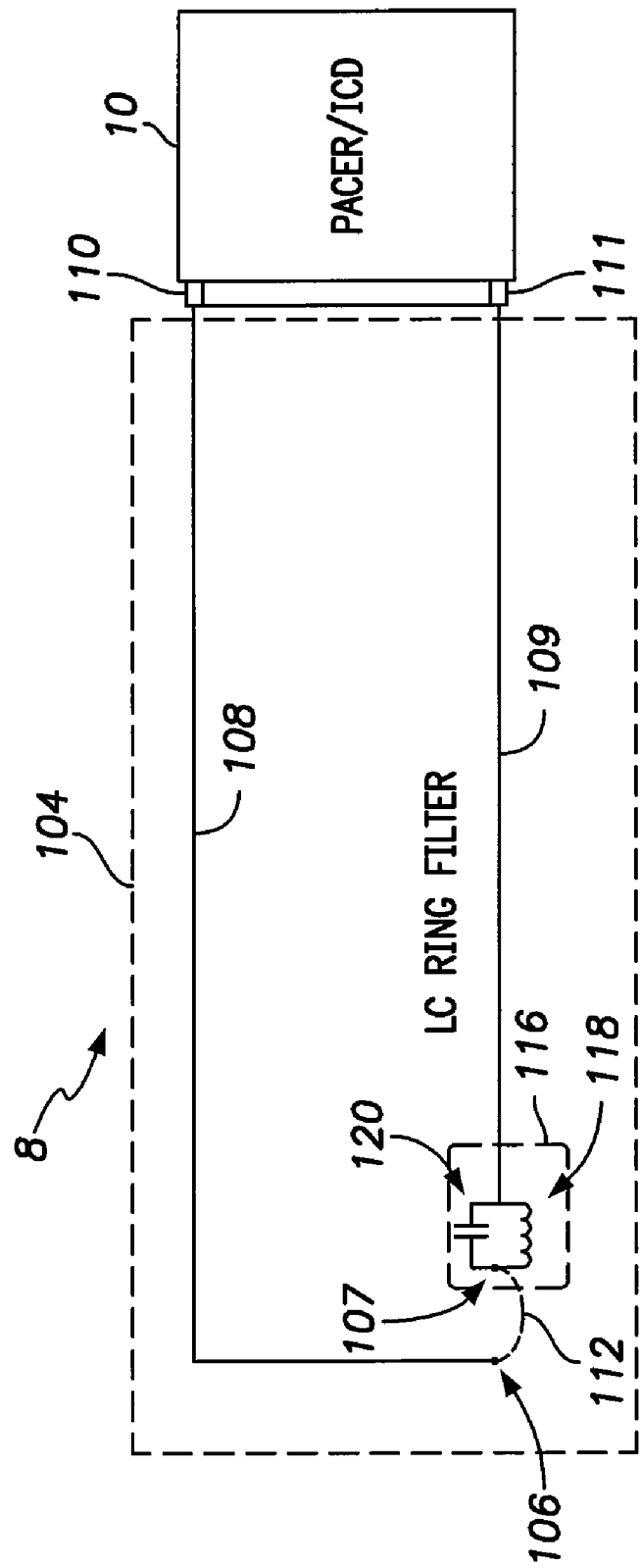
FIG. 2 is a block diagram, partly in schematic form, illustrating a bipolar lead for use with the pacer/ICD of FIG. 1 wherein an LC filtering element is mounted along a ring conductor to reduce tip heating during an MRI, and also illustrating a pacer/ICD connected to the lead.

FIG. 2 illustrates implantable system 8 with a pacer/ICD or other implantable medical device 10 equipped with a bipolar coaxial lead 104. The bipolar lead includes a tip electrode 106 electrically connected to the pacer/ICD via a tip conductor 108 coupled to a tip connector or terminal 110 of the pacer/ICD. The bipolar lead also includes a ring electrode 107 electrically connected to the pacer/ICD via a ring conductor 109 coupled to a ring connector or terminal 111 of the pacer/ICD. Depending upon the particular implementation, during pacing/sensing, the tip electrode may be more negative than the ring, or vice versa. A conducting path 112 between tip electrode 106 and ring electrode 107 is provided through patient tissue (typically cardiac tissue.) At the location of the ring electrode, a ring-based parallel LC filter 116 is provided, which includes an inductive element 118 and a capacitive element 120, formed in parallel. The parallel LC filter is configured to provide a substantial amount of bandstop filtering at the radio frequencies associated with MRI machines. As will be further explained, at least a portion of the ring electrode can form all or part of the capacitive element of the filter, to help reduce the package size of the parallel LC filter.

As to the RF bandstop filtering, during an MRI one or more current loops might be induced within the lead (and within any circuit components within the pacer/ICD that electrically connect terminals 110 and 111). The parallel LC filter is configured to filter frequencies associated with such current loops to decrease the magnitude thereof. Without the parallel LC filter, strong current loops might pass through patient tissue between the tip and ring electrodes before returning to the pacer/ICD, causing considerable resistive heating at the electrodes and in the intervening tissue. As explained above, such heating can damage patient tissue and interfere with pacing and sensing. In addition, as noted, the current loops can cause MRI-induced pacing.

With parallel LC filter 116, however, any such current loops are greatly diminished, thereby reducing a significant source of lead heating as well as preventing or limiting MRI-induced pacing. Although not shown, RF shielding and/or MRI responsive switches can also be provided to further reduce lead heating. See, for example, the various patents and patent applications cited above. If one or more atrial leads are provided, parallel LC filters can be provided along those leads as well. Different types/sizes of parallel LC filters may be provided within atrial leads as compared to ventricular leads, with the filters of ventricular leads being generally more robust than the LC filters of the atrial leads since, typically, larger currents are induced in ventricular leads than in atrial leads during an MRI.

Ring-mounted LC Filter Examples

Figure 3:
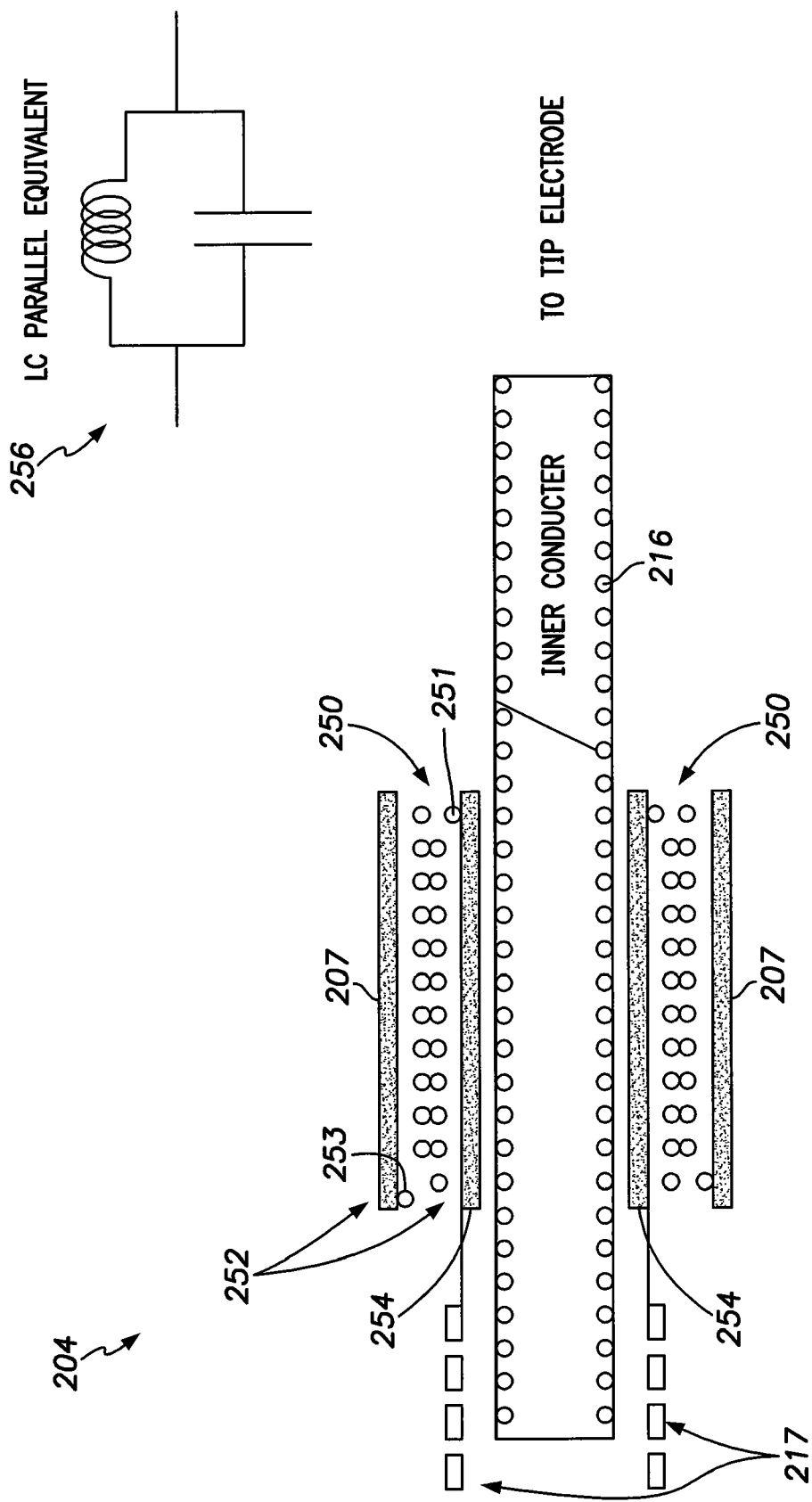
FIG. 3 is a simplified side cross-sectional view of a portion of another coaxial embodiment of a bipolar lead of FIG. 2, wherein parallel LC filtering is achieved via a pair of tube-shaped capacitive elements (coaxial with the lead), which encircle an inductive coil at the location of the ring electrode.

FIG. 3 illustrates a coaxial implementation with parallel LC filtering wherein a pair of tube-shaped capacitive elements is provided within the lead at the location of the ring electrode. The pair of capacitive elements encloses or encircles an inductive coil to provide LC bandstop filtering. More specifically, FIG. 3 shows a portion of a coaxial lead 204 with an outer (ring) conductor 217 (which may be in the form of a coil) and an inner (tip) conductor 216 (which may also be in the form of a coil). A distal end of the outer conductor is coupled to a coiled inductor made of insulated wires 250, which is referred to herein as the "ring electrode inductor" since it is located inside a ring electrode 207 of the lead. In this example, ring electrode 207 also serves as the outer capacitive element of a coaxial capacitor 252, along with an inner capacitive element 254. Note that both ring electrode 207 and inner capacitive element 254 are conducting tubes or shafts, which are coaxial with one another and with the axis of the lead, and which together form a capacitor that surrounds, encircles, sandwiches, envelops or otherwise encloses inductor 250. This provides for a parallel LC filter arrangement, as shown by LC equivalent circuit 256.

Note that the inner conductor 216 passes through the inside of the inner capacitive element 254 to a tip electrode (not shown in FIG. 3.) Coiled inductor 250 is electrically coupled at a distal end 251 with inner capacitive element 254 and is also electrically coupled at a proximal end 253 with ring electrode 207, which allows for transmission of relatively low frequency pacing/sensing/shocking signals to/from patient tissues via the ring conductor.

With this arrangement, element 207 serves as both the ring electrode of the lead and the outer capacitive element of capacitor 252. In other implementations, a separate ring electrode can be mounted external to outer capacitive element 207 (see, e.g., FIG. 4) but, for the sake of minimizing the size of the LC filter arrangement, in this particular implementation, capacitive element 207 serves as both the ring electrode and the outer element of capacitor 252. Note that FIG. 3 is a simplified view that shows only selected components of the lead and does not illustrate all features or components, such as an outer sheath of insulation, etc.

Otherwise routine testing and experimentation may be performed to determine preferred parameters for configuring the various capacitive and inductive elements—such as inner diameters, outer diameters, length, number of turns, etc.—for use in a particular lead so as to achieve a desired impedance at particular RF signal frequencies, such as those of MRIs. In this regard, in designs of coiled inductors without adjacent parallel capacitors, modeling and network analyzer tests have shown that a five layer coil with 28 turns/layer (for a total of 140 turns) is typically appropriate to achieve an SRF of 64 MHz, where the silver-cored MP35N referred as DFT (75% Ag in core and 25% Ag for outer shell) wire diameter is 2 mils (44 gauge) and ETFE coating is 0.5 mil. Alternatively, seven layers with 19 turns/layer are typically appropriate for SRF=64 MHz. For the case with capacitors built into the structure as shown in FIG. 3, required L for resonance is smaller according to $2\pi f=1/\sqrt{(LC)}$. A lower required L value implies fewer turns for the inductor or less space/smaller size. If the space is kept the same, this implies that a larger wire diameter or a multi-fillar may be used. In other words, there are package size advantages to the LC design of FIG. 4. Additionally, greater electrical and mechanical reliability can typically be achieved, as there are a variety of ways of making connections between the various capacitive elements and inductor wires.

Figure 4:
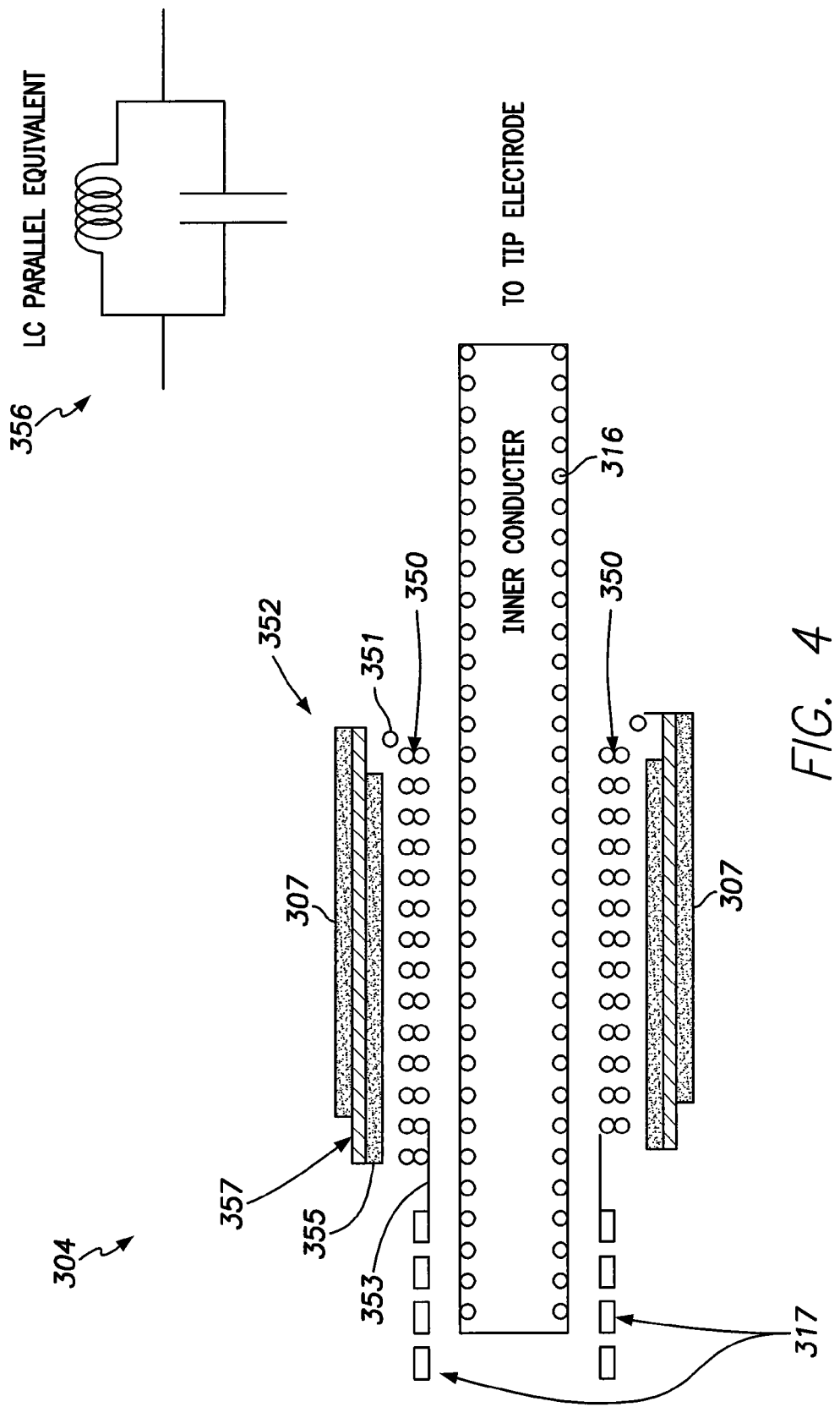
FIG. 4 is a simplified side cross-sectional view of an alternative embodiment of the parallel LC filter arrangement of FIG. 3, with a single tube-shaped capacitive element provided inside the ring electrode.

FIG. 4 illustrates an alternative coaxial implementation with a parallel LC filter for use at the location of the ring electrode. More specifically, FIG. 4 shows a portion of a coaxial lead 304 with an outer ring conductor 317 and an inner tip conductor 316. The distal end of the outer ring conductor is coupled to a coiled inductor 350 formed of insulated wires, internal to a tube-shaped capacitive element 307. Parallel tube-shaped capacitive elements 355 and 307 along with dielectric layer 357 form a capacitor 352 fitted inside a ring electrode (not separately shown in FIG. 4). Note that, in this embodiment, the ring electrode can additionally or alternatively be used to form all or a portion of the capacitor (i.e. element 307 can be used as the ring electrode). Note also that both parallel capacitive elements 307 and 355 also function as an effective heat spreader.

Thus, capacitor 352 is a conducting tube or shaft, which is coaxial with the axis of the lead and which surrounds, envelops, encircles or encloses inductor 350. This again provides for a parallel LC filter arrangement, as shown by LC equivalent circuit 356. Note also that insulated inductor 350 is electrically coupled at a distal end 351 of capacitor 352 and is also electrically coupled at a proximal end 353 with outer conductor 317, which allows for transmission of the relatively low frequency pacing/sensing/shocking signals to/from patient tissues via the capacitor and the ring conductor.

Insofar as mounting is concerned, inductor 350 can be mounted to a hollow or donut-shaped ceramic or dielectric substrate 357 between capacitive plates 307 and 355. The inductor itself can be coiled or spiral. Again, otherwise routine testing and experimentation may be performed to determine preferred parameters for configuring the various capacitive and inductive elements—such as inner diameters, outer diameters, length, number of turns, etc.—for use in a particular lead so as to achieve a desired impedance at particular RF signal frequencies, such as those of MRIs. As with other figures herein, FIG. 4 is a simplified view that shows only selected components of the lead and does not illustrate all features or components. Note that the configuration in FIG. 4 can generally provide better capacitance than that in FIG. 3, in part because of the added dielectric layer.

Figure 5:
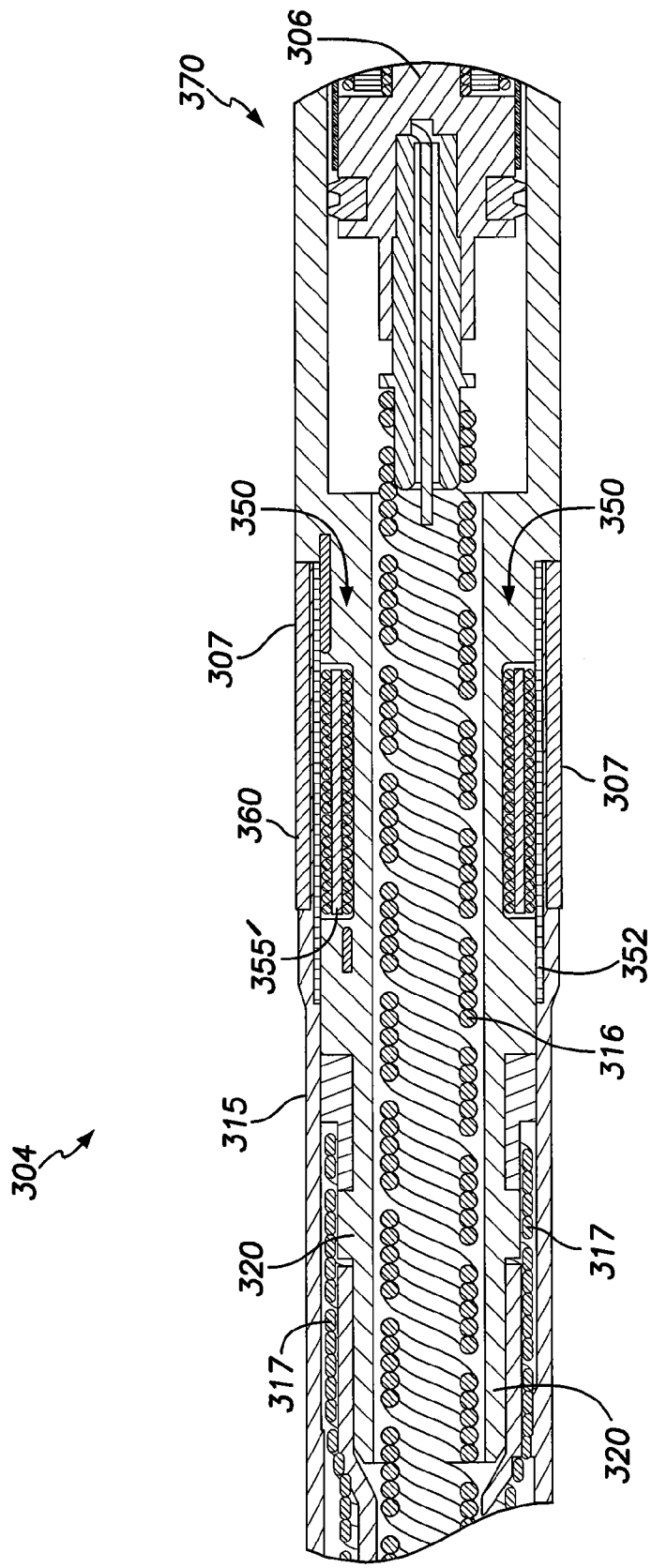
FIG. 5 is a more detailed cross-sectional view of the embodiment of FIG. 4.

FIG. 5 provides a more detailed view of the embodiment of FIG. 4 (with slight modifications.) Here, the substrate 355' on which the inductor 350 is mounted is between inner and outer turns of the inductor. The figure also illustrates a portion of a tip assembly 306 for mounting a tip electrode. Various other components are also shown, including various insulating layers such as outer sheath 315 and inner insulator 320. Still further, the figure also specifically illustrates a ring electrode 360, which is electrically coupled to the LC filter.

Note that the configurations in FIGS. 3 and 4 also are applicable for tip inductors in both passive and active fixture leads, where element 351 is connected to tip electrode.

Tip-mounted LC Filter Examples

Figure 6:
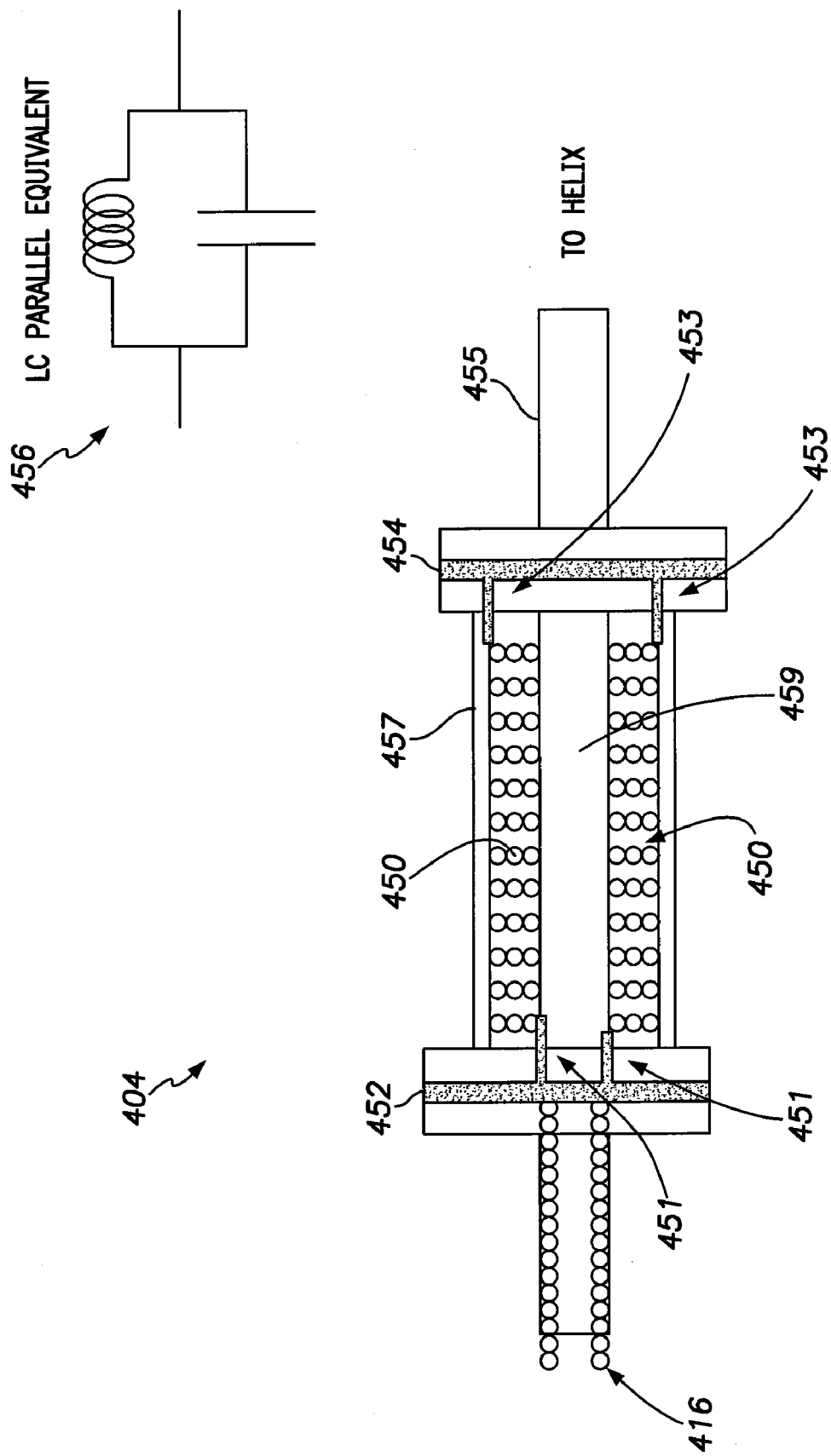
FIG. 6 is a simplified side cross-sectional view of a portion of yet another coaxial embodiment of a bipolar lead of FIG. 1, wherein parallel LC filtering is achieved via a pair of circular capacitive plates (perpendicular to the axis of the lead), which sandwich an inductive coil provided along the tip conductor near the tip of the lead.
Figure 7:
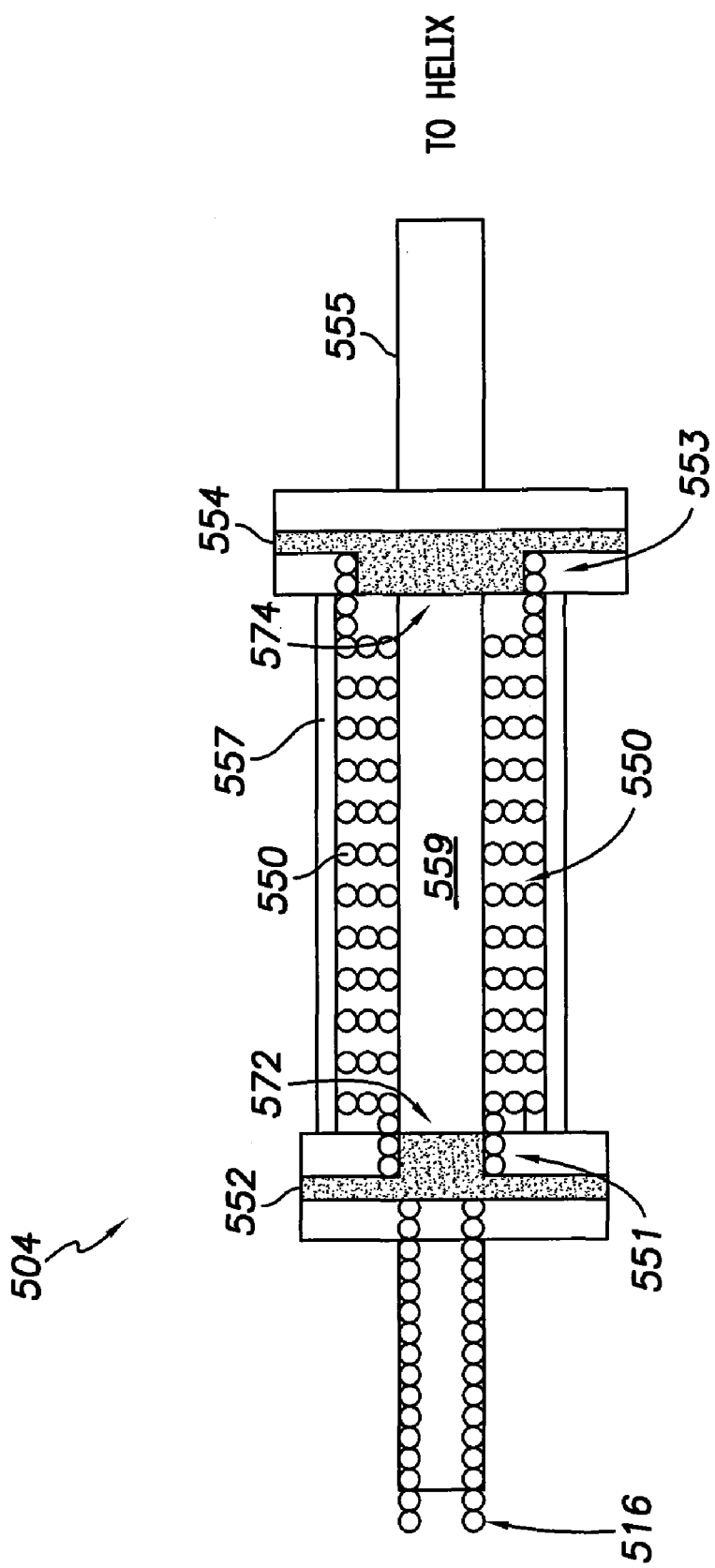
FIG. 7 is a simplified side cross-sectional view of an alternative embodiment of the parallel LC filter arrangement of FIG. 6, with a different configuration for the electrical connection between capacitive plates and inductive coil.
Figure 8:
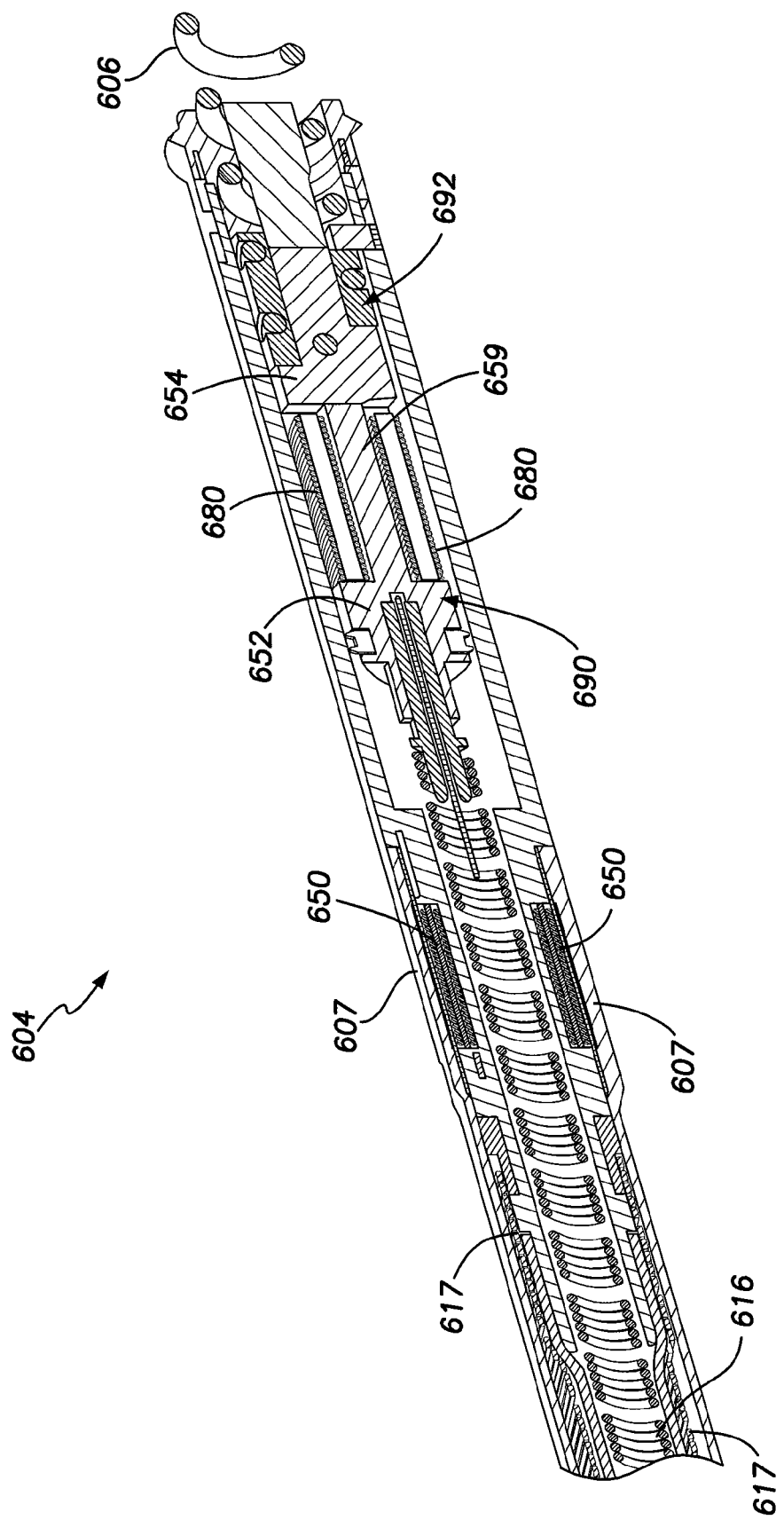
FIG. 8 illustrates an implementation having features drawn from the embodiments of FIGS. 3-7.

Turning now to FIGS. 6-8, various embodiments wherein the parallel LC filer is additionally or alternatively mounted in or near the tip assembly of the lead will be described.

FIG. 6 illustrates a coaxial implementation with parallel LC filtering wherein a pair of substantially circular capacitive plates is provided along the tip conductor within the lead at a location distal to the ring electrode (which is not shown in this particular figure.) The pair of capacitive plates (which are perpendicular the axis of the lead) sandwich an inductive coil (which is coaxial with the lead) to provide parallel LC band-stop filtering. More specifically, FIG. 6 shows a portion of a coaxial lead 404 with an inner tip conductor 416. (The outer ring conductor, which terminates at the ring electrode, is not shown in the figure.) The inner conductor is coupled to a first or proximal capacitive plate 452, which is in turn coupled to a proximal end of an inductor 450 (which is referred to herein as the "tip electrode inductor" since it is located near the tip of the lead.) A distal end of the inductor is coupled to a second or distal capacitive plate 454, which is in turn coupled to a conductor 455 that leads to a helical tip electrode (not shown in FIG. 6.)

Plates 452 and 454 are parallel to one another and perpendicular to the axis of the lead. Together the two plates form a capacitor that sandwiches inductor 450. This provides for a parallel LC filter arrangement, as shown by LC equivalent circuit 456. Note that inductor 450 is electrically coupled at its proximal end with capacitive element 452 via one or more coupling elements 451. The inductor is also electrically coupled at its distal end with capacitive element 454 via one or more coupling elements 453. Additionally, as shown, the turns of the inductor may be formed around an inner insulating core or shaft 459 and enclosed within an outer insulating tube or shaft 457.

FIG. 7 illustrates an alternative coaxial implementation with parallel LC filtering wherein, again, a pair of circular capacitive plates is provided along the tip conductor, which sandwich a tip inductor. A different means of electrical connection is provided between the inductor and the capacitive plates as compared to the preceding embodiment. More specifically, FIG. 7 shows a portion of a coaxial lead 504 with an inner conducting coil 516. The inner conducting coil is coupled to a first capacitive plate 552, which is in turn coupled to an inductor 550. A distal end of the inductor is coupled to a second capacitive plate 554, which is in turn coupled to a conductor 555 that leads to a helical tip electrode. Together, plates 552 and 554 form a capacitor that sandwiches inductor 550, as in FIG. 6. However, in this embodiment, plates 552 and 554 include mounting shafts or cores 572 and 574, respectively. Inductor 550 is electrically coupled at a proximal end to capacitive element 552 by wrapping proximal coils 551 around core 572. Inductor 550 is also electrically coupled at a distal end to capacitive element 554 by wrapping distal coils 553 around core 574. This provides for an especially sturdy and reliable electrical connection between inductor and capacitor. Additionally, as shown, the turns of the inductor may be formed around an inner insulating core or shaft 559 and enclosed within an outer insulating tube or shaft 557.

By using this type of capacitive design, with about the same space as coil inductor designs without capacitors, multi-fillar inductors or bigger wire diameters can be used to increase redundancy for better electrical and mechanical reliability. The use of metal plates for capacitors also provides for a good heat sink for the inductor wire to participate. This allows, e.g., inductors to better withstand the higher currents of external defibrillation shocks.

Additionally, as shown, the turns of the inductor may be formed around an inner insulating core or shaft 559 and enclosed within an outer insulating tube or shaft 557.

FIG. 8 illustrates yet another coaxial implementation with parallel LC filtering. Here, a ring inductor 650 (of the type used in FIGS. 3-5) is employed, along with a tip inductor 680 (of the type used in FIGS. 6-7.) More specifically, FIG. 8 shows a portion of a coaxial lead 604 with an inner tip conducting coil 616 and an outer ring conducting coil 617. The outer coil is coupled to an insulated inductor 650, which is located inside the ring electrode 607 of the lead. The inner conducting coil 616 passes through the inside of the ring inductor 650 to a tip electrode 606 (which is helical) via a tip assembly that includes a tip inductor 680 sandwiched between a pair of capacitive elements 652 and 654. Tip inductor 680 is formed around a non-conducting shaft 659, which separates the pair of capacitive elements. An electrical connection from the tip conductor 616 to capacitive element 652 is provided at 690. An electrical connection from capacitive element 654 to helical tip 606 of the lead is provided at 692.

Again, otherwise routine testing and experimentation may be performed to determine preferred parameters for configuring the various capacitive and inductive elements—such as inner diameters, outer diameters, length, number of turns, etc.—for use in a particular lead so as to achieve a desired impedance at particular RF signal frequencies, such as those of MRIs.

The various configurations described above can be exploited for use with a wide variety of implantable medical systems. For the sake of completeness, a detailed description of an exemplary pacer/ICD and lead system will now be provided.

Exemplary Pacer/ICD/Lead System

FIG. 9 provides a simplified diagram of the pacer/ICD of FIG. 1. The pacer/ICD is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 812 by way of a right atrial lead 820 having an atrial tip electrode 822 and an atrial ring electrode 823 implanted in the atrial appendage. Pacer/ICD 10 is also in electrical communication with the heart by way of a right ventricular lead 830 having, in this embodiment, a ventricular tip electrode 832, a right ventricular ring electrode 834, a right ventricular (RV) coil electrode 836. Typically, the right ventricular lead 830 is transvenously inserted into the heart so as to place the RV coil electrode 836 in the right ventricular apex. Accordingly, the right ventricular lead is capable of receiving cardiac signals, and delivering stimulation in the form of pacing and shock therapy to the right ventricle. A parallel LC bandpass filter, configured as described above, is positioned within and along distal portions of lead 830 (such as at the location of the ring electrode or near the tip electrode) so as to reduce lead heating. The filter is not shown in this particular figure, as it is internal to the lead. A similar parallel LC bandpass filter may be provided within RA lead 820.

To sense left atrial and ventricular cardiac signals and to provide left chamber pacing therapy, pacer/ICD 10 is coupled to a "coronary sinus" lead 824 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 824 is designed to receive atrial and ventricular cardiac signals and to deliver left ventricular pacing therapy using at least a left ventricular tip electrode 826 and a left ventricular ring electrode 829 and to deliver left atrial pacing therapy using at least a left atrial ring electrode 827, and shocking therapy using at least an SVC coil electrode 828. A parallel LC bandpass filter, configured as described above, is positioned within and along distal portions of lead 824 (such as at the location of the ring electrode or near the tip electrode) so as to reduce lead heating. The filter is shown not shown in this particular figure, as it is internal to the lead.

With this lead configuration, biventricular pacing can be performed. Although only three leads are shown in FIG. 9, it should also be understood that additional stimulation leads (with one or more pacing, sensing and/or shocking electrodes) may be used in order to efficiently and effectively provide pacing stimulation to the left side of the heart or atrial cardioversion and/or defibrillation. The filters reduce lead heating during MRIs or in the presence of other sources of strong RF fields.

Figure 10:
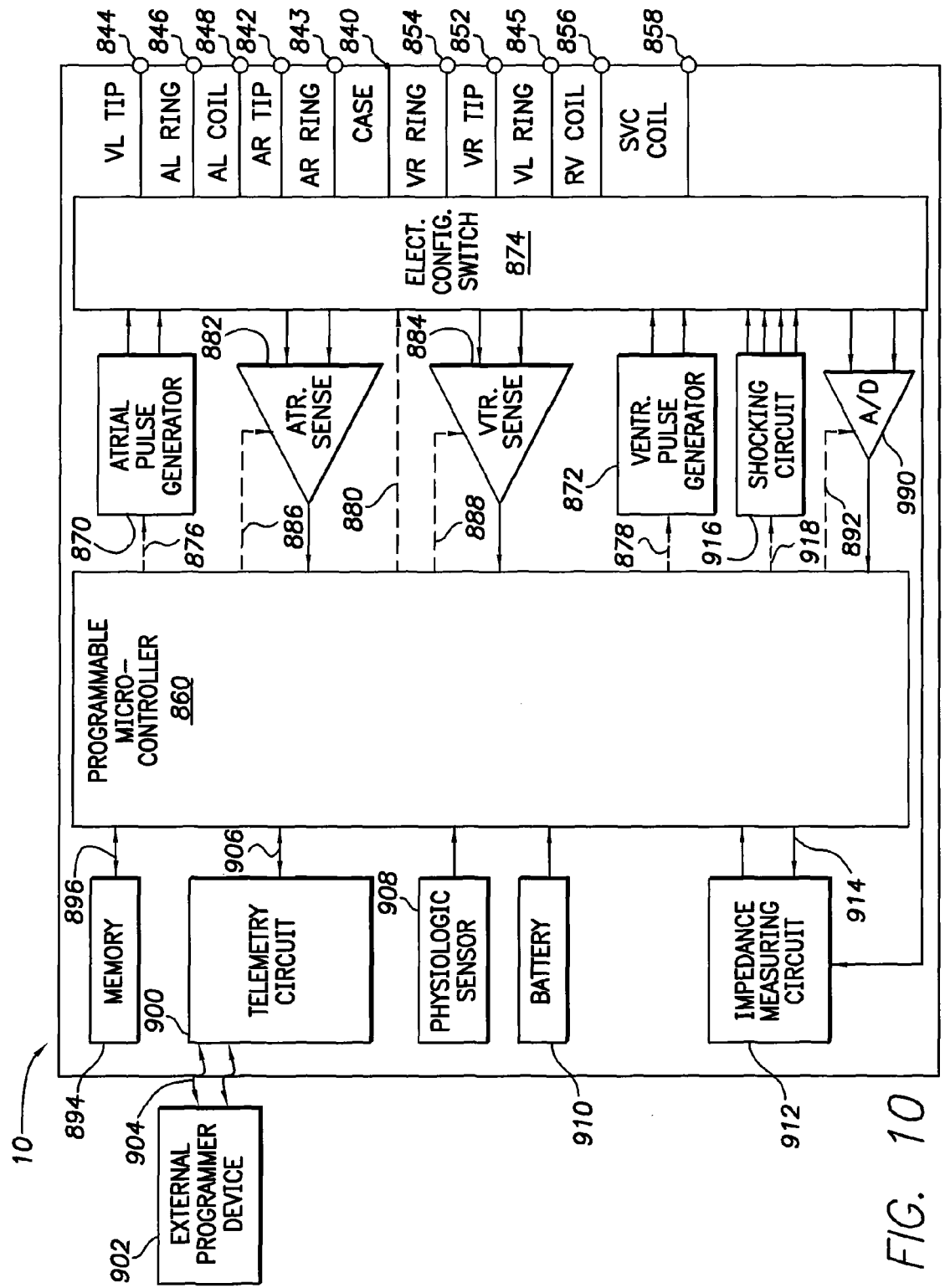
FIG. 10 is a functional block diagram of the pacer/ICD of FIG. 6, illustrating basic circuit elements that provide cardioversion, defibrillation and/or pacing stimulation in four chambers of the heart.

A simplified block diagram of internal components of pacer/ICD 10 is shown in FIG. 10. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 840 for pacer/ICD 10, shown schematically in FIG. 10, is often referred to as the "can", "case" or "case electrode" and may be programmably selected to act as the return electrode for all "unipolar" modes. The housing 840 may further be used as a return electrode alone or in combination with one or more of the coil electrodes, 828, 836 and 838, for shocking purposes. The housing 840 further includes a connector (not shown) having a plurality of terminals, 842, 843, 844, 845, 846, 848, 852, 854, 856 and 858 (shown schematically and, for convenience, the names of the electrodes to which they are connected are shown next to the terminals). As such, to achieve right atrial sensing and pacing, the connector includes at least a right atrial tip terminal ($A_R$ TIP) 842 adapted for connection to the atrial tip electrode 822 and a right atrial ring ($A_R$ RING) electrode 843 adapted for connection to right atrial ring electrode 823. To achieve left chamber sensing, pacing and shocking, the connector includes at least a left ventricular tip terminal ($V_L$ TIP) 844, a left ventricular ring terminal ($V_L$ RING) 845, a left atrial ring terminal ($A_L$ RING) 846, and a left atrial shocking terminal ($A_L$ COIL) 848, which are adapted for connection to the left ventricular ring electrode 826, the left atrial tip electrode 827, and the left atrial coil electrode 828, respectively. To support right chamber sensing, pacing and shocking, the connector further includes a right ventricular tip terminal ($V_R$ TIP) 852, a right ventricular ring terminal ($V_R$ RING) 854, a right ventricular shocking terminal ($R_v$ COIL) 856, and an SVC shocking terminal (SVC COIL) 858, which are adapted for connection to the right ventricular tip electrode 832, right ventricular ring electrode 834, the RV coil electrode 836, and the SVC coil electrode 838, respectively.

At the core of pacer/ICD 10 is a programmable microcontroller 860, which controls the various modes of stimulation therapy. As is well known in the art, the microcontroller 860 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 860 includes the ability to process or monitor input signals (data) as controlled by a program code stored in a designated block of memory. The details of the design and operation of the microcontroller 860 are not critical to the invention. Rather, any suitable microcontroller 860 may be used that carries out the functions described herein. The use of microprocessor-based control circuits for performing timing and data analysis functions are well known in the art.

As shown in FIG. 10, an atrial pulse generator 870 and a ventricular pulse generator 872 generate pacing stimulation pulses for delivery by the right atrial lead 820, the right ventricular lead 830, and/or the coronary sinus lead 824 via an electrode configuration switch 874. It is understood that in order to provide stimulation therapy in each of the four chambers of the heart, the atrial and ventricular pulse generators, 870 and 872, may include dedicated, independent pulse generators, multiplexed pulse generators or shared pulse generators. The pulse generators, 870 and 872, are controlled by the microcontroller 860 via appropriate control signals, 876 and 878, respectively, to trigger or inhibit the stimulation pulses.

The microcontroller 860 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 874 includes a plurality of switches for connecting the desired electrodes to the appropriate I/O circuits, thereby providing complete electrode programmability. Accordingly, the switch 874, in response to a control signal 880 from the microcontroller 860, determines the polarity of the stimulation pulses (e.g., unipolar, bipolar, combipolar, etc.) by selectively closing the appropriate combination of switches (not shown) as is known in the art.

Atrial sensing circuits 882 and ventricular sensing circuits 884 may also be selectively coupled to the right atrial lead 820, coronary sinus lead 824, and the right ventricular lead 830, through the switch 874 for detecting the presence of cardiac activity in each of the four chambers of the heart. Accordingly, the atrial (ATR. SENSE) and ventricular (VTR. SENSE) sensing circuits, 882 and 884, may include dedicated sense amplifiers, multiplexed amplifiers or shared amplifiers. The switch 874 determines the "sensing polarity" of the cardiac signal by selectively closing the appropriate switches, as is also known in the art. In this way, the clinician may program the sensing polarity independent of the stimulation polarity. Each sensing circuit, 882 and 884, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain and/or sensitivity control enables pacer/ICD 10 to deal effectively with the difficult problem of sensing the low amplitude signal characteristics of atrial or ventricular fibrillation. The outputs of the atrial and ventricular sensing circuits, 882 and 884, are connected to the microcontroller 860 which, in turn, are able to trigger or inhibit the atrial and ventricular pulse generators, 870 and 872, respectively, in a demand fashion in response to the absence or presence of cardiac activity in the appropriate chambers of the heart.

For arrhythmia detection, pacer/ICD 10 utilizes the atrial and ventricular sensing circuits, 882 and 884, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "Fib-waves") are then classified by the microcontroller 860 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 890. The data acquisition system 890 is configured to acquire intracardiac electrogram signals, convert the raw analog data into a digital signal, and store the digital signals for later processing and/or telemetric transmission to an external device 902. The data acquisition system 890 is coupled to the right atrial lead 820, the coronary sinus lead 824, and the right ventricular lead 830 through the switch 874 to sample cardiac signals across any pair of desired electrodes. The microcontroller 860 is further coupled to a memory 894 by a suitable data/address bus 896, wherein the programmable operating parameters used by the microcontroller 860 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 894 through a telemetry circuit 900 in telemetric communication with an external device 902, such as a programmer, transtelephonic transceiver or a diagnostic system analyzer, or a bedside monitoring system. The telemetry circuit 900 is activated by the microcontroller by a control signal 906. The telemetry circuit 900 advantageously allows IEGMs and other electrophysiological signals and/or hemodynamic signals and status information relating to the operation of pacer/ICD 10 (as stored in the microcontroller 860 or memory 894) to be sent to the external programmer device 902 through an established communication link 904.

Pacer/ICD 10 further includes an accelerometer or other physiologic sensor 908, commonly referred to as a "rate-responsive" sensor because it is typically used to adjust pacing stimulation rate according to the exercise state of the patient. However, the physiological sensor 908 may further be used to detect changes in cardiac output, changes in the physiological condition of the heart, or diurnal changes in activity (e.g., detecting sleep and wake states) and to detect arousal from sleep. Accordingly, the microcontroller 860 responds by adjusting the various pacing parameters (such as rate, AV Delay, V-V Delay, etc.) at which the atrial and ventricular pulse generators, 870 and 872, generate stimulation pulses. While shown as being included within pacer/ICD 10, it is to be understood that the physiologic sensor 908 may also be external to pacer/ICD 10, yet still be implanted within or carried by the patient. A common type of rate responsive sensor is an activity sensor incorporating an accelerometer or a piezoelectric crystal, which is mounted within the housing 840 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 910, which provides operating power to all of the circuits shown in FIG. 10. The battery 910 may vary depending on the capabilities of pacer/ICD 10. If the system only provides low voltage therapy, a lithium iodine or lithium copper fluoride cell may be utilized. For pacer/ICD 10, which employs shocking therapy, the battery 910 must be capable of operating at low current drains for long periods, and then be capable of providing high-current pulses (for capacitor charging) when the patient requires a shock pulse. The battery 910 must also have a predictable discharge characteristic so that elective replacement time can be detected. Accordingly, pacer/ICD 10 is preferably capable of high voltage therapy and appropriate batteries.

As further shown in FIG. 10, pacer/ICD 10 is shown as having an impedance measuring circuit 912 which is enabled by the microcontroller 860 via a control signal 914. Various uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, measuring lead resistance, etc. The impedance measuring circuit 120 is advantageously coupled to the switch 94 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 860 further controls a shocking circuit 916 by way of a control signal 918. The shocking circuit 916 generates shocking pulses of low (up to 0.5 joules), moderate (0.5-11 joules) or high energy (11 to at least 40 joules), as controlled by the microcontroller 860. Such shocking pulses are applied to the heart of the patient through at least two shocking electrodes, and as shown in this embodiment, selected from the left atrial coil electrode 828, the RV coil electrode 836, and/or the SVC coil electrode 838. The housing 840 may act as an active electrode in combination with the RV electrode 836, or as part of a split electrical vector using the SVC coil electrode 838 or the left atrial coil electrode 828 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 860 is capable of controlling the synchronous or asynchronous delivery of the shocking pulses.

What have been described are systems and methods for use with a set of pacing/sensing leads for use with a pacer/ICD. Principles of the invention may be exploiting using other implantable systems or in accordance with other techniques. Thus, while the invention has been described with reference to particular exemplary embodiments, modifications can be made thereto without departing from the scope of the invention.

What is claimed is:

1. A lead for use with an implantable medical device for implant within a patient, the lead comprising:
    an electrode for placement adjacent patient tissues, with at least a portion of the electrode forming a capacitive element;
    a conductor operative to route signals along the lead between the electrode and the implantable medical device; and
    an inductive element provided in parallel with the capacitive element of the electrode to provide a parallel inductive-capacitive (LC) bandstop filter configured to filter radio-frequency (RF) signals.

2. The lead of claim 1 wherein the capacitive element is configured with parallel elements that encircle at least a portion of the inductive element.

3. The lead of claim 2 wherein the conductor is a ring conductor of the lead and wherein the electrode is a ring electrode.

4. The lead of claim 3 wherein the lead further includes a tip conductor coupled to a tip electrode.

5. The lead of claim 4 wherein the lead is bi-polar.

6. The lead of claim 4 wherein the lead is coaxial.

7. The lead of claim 4 wherein the inductive element is formed of insulated wires.

8. The lead of claim 4 wherein the capacitive element includes:
    an outer tube-shaped element coaxial with the lead and electrically connected to one end of the encircled portion of the inductor; and
    an inner tube-shaped element coaxial with the lead and electrically connected to an opposing end of the encircled portion of the inductor.

9. The lead of claim 8 wherein the inner tip conductor is fitted through a center shaft of the inner tube-shaped element.

10. The lead of claim 8 wherein the outer tube-shaped element comprises at least a portion of the ring electrode.

11. The lead of claim 7 wherein the capacitive element includes:
    a tube-shaped element coaxial with the lead and electrically connected to one end of the encircled portion of the inductor; and
    wherein the ring electrode is mounted to an exterior surface of the tube-shaped element.

12. The lead of claim 11 wherein the encircled portion of the inductor is one of a coiled inductor or a spiral inductor.

13. The lead of claim 11 wherein the encircled portion of the inductor is formed on a dielectric substrate.

14. The lead of claim 11 wherein the encircled portion of the inductor is formed on a printed ceramic.

15. The lead of claim 11 wherein a first capacitive-inductive element is provided along the lead at the location of the ring electrode and wherein a second capacitive-inductive element is provided along the lead distal to the location of the ring electrode.

16. The lead of claim 15 wherein the first and second capacitive-inductive elements are configured to provide different self-resonance frequencies (SRFs).

17. The lead of claim 1 wherein the capacitive element provided in parallel with the inductor are configured to provide LC bandstop filtering at one or more of about 64 MHz and about 128 MHz.

18. An implantable medical system for implant within a patient comprising:
an implantable cardiac rhythm management device; and
a lead for use with the implantable medical device wherein the lead includes an electrode for placement adjacent patient tissues with at least a portion of the electrode forming a capacitive element, a conductor operative to route signals along the lead between the electrode and the implantable medical device, and an inductive element provided in parallel with the capacitive element of the electrode to provide a parallel inductive-capacitive (LC) bandstop filter configured to filter radio-frequency (RF) signals.

19. A lead for use with an implantable medical device for implant within a patient, the lead comprising:
a tip electrode for placement adjacent patient tissues;
a tip conductor operative to route signals along the lead between the tip electrode and the implantable medical device; and
a parallel inductive-capacitive (LC) bandstop filter configured to filter radio-frequency (RF) signals, the filter having a capacitive element and an inductive element wherein the capacitive element is configured with parallel plate elements that sandwich at least a portion of the inductor.

20. The lead of claim 19 wherein the capacitive element includes:
a proximal plate mounted perpendicular a longitudinal axis of the lead and electrically connected to a proximal end of a portion of the tip electrode; and
a distal plate mounted perpendicular a longitudinal axis of the lead and electrically connected to a distal end of the portion of the tip conductor.

21. The lead of claim 20
wherein the proximal plate includes a cylindrical mounting shaft coaxial with the lead and wherein the proximal end of the portion of the tip electrode is fitted around the mounting shaft of the proximal plate to provide an electrical connection therebetween; and
wherein the distal plate includes a cylindrical mounting shaft coaxial with the lead and wherein the distal end of the portion of the tip conductor is fitted around the mounting shaft of the distal plate to provide an electrical connection therebetween.

* * * * *